(12) United States Patent
Greenberg et al.

(10) Patent No.: US 10,335,234 B2
(45) Date of Patent: *Jul. 2, 2019

(54) ABLATION CANNULA AND KIT WITH INSERT

(71) Applicant: ORTHOPAEDIC DEVELOPMENT LLC, Lake Worth, FL (US)

(72) Inventors: Steven M. Greenberg, Boca Raton, FL (US); Scott S. Katzman, Port St. Lucie, FL (US); Chris J. Carron, Bloomsdale, MO (US)

(73) Assignee: ORTHOPAEDIC DEVELOPMENT, LLC, Lake Worth, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/334,260

(22) Filed: Oct. 25, 2016

(65) Prior Publication Data

US 2017/0035510 A1 Feb. 9, 2017

Related U.S. Application Data

(60) Continuation of application No. 14/287,369, filed on May 27, 2014, now Pat. No. 9,474,577, which is a
(Continued)

(51) Int. Cl.
*A61B 17/34* (2006.01)
*A61B 18/22* (2006.01)
(Continued)

(52) U.S. Cl.
CPC .......... *A61B 18/22* (2013.01); *A61B 17/3417* (2013.01); *A61B 18/1477* (2013.01);
(Continued)

(58) Field of Classification Search
CPC . A61B 17/34; A61B 17/3403; A61B 17/3415; A61B 17/3417; A61B 17/3421;
(Continued)

(56) References Cited

U.S. PATENT DOCUMENTS 6,224,566 B1 * 5/2001 Loeb ................. A61M 25/0084
604/20
6,258,083 B1 * 7/2001 Daniel ............... A61B 1/00098
606/15

(Continued)

*Primary Examiner* — Ahmed M Farah
(74) *Attorney, Agent, or Firm* — Steven M. Greenberg, Esq.; Shutts & Bowen LLP

(57) ABSTRACT

An ablation tool includes a trocar and cannula with a hollow shaft. The hollow shaft is configured to permit passage of the trocar therethrough and has a proximal segment and a distal segment. The distal segment includes a distal tip aligned with the hollow shaft of the cannula to permit passage of the trocar within the hollow shaft of the cannula, and has tissue-adhering irregular surfaces protruding therefrom. An auxiliary port extends from an exterior surface of the cannula and defines a hollow passageway into the hollow shaft. Notably, an insert is provided as part of the tool. The insert defines a hollow shaft and is adapted to be inserted into the hollow shaft of the cannula and includes a diameter of less than an interior diameter of the hollow shaft of the insert so as to permit passage of a laser fiber through the hollow shaft of the insert. An auxiliary port extends from an exterior surface of the insert defining a hollow passageway into the hollow shaft of the insert.

7 Claims, 2 Drawing Sheets

Related U.S. Application Data continuation-in-part of application No. 13/770,859, filed on Feb. 19, 2013, now Pat. No. 8,734,435, which is a continuation-in-part of application No. 11/101,221, filed on Apr. 7, 2005, now Pat. No. 8,376,931, which is a division of application No. 10/278,405, filed on Oct. 23, 2002, now Pat. No. 6,902,526.

(51) Int. Cl.
*A61B 18/20* (2006.01)
*A61B 18/24* (2006.01)
*A61B 18/14* (2006.01)
*A61B 18/00* (2006.01)

(52) U.S. Cl.
CPC .............. *A61B 18/20* (2013.01); *A61B 18/24* (2013.01); *A61B 2018/00339* (2013.01); *A61B 2018/00434* (2013.01); *A61B 2018/00565* (2013.01); *A61B 2018/00577* (2013.01); *A61B 2018/00982* (2013.01); *A61B 2018/206* (2013.01); *A61B 2217/005* (2013.01); *A61B 2217/007* (2013.01); *A61B 2218/002* (2013.01); *A61B 2218/007* (2013.01)

(58) Field of Classification Search
CPC .... A61B 2017/3433; A61B 2017/3445; A61B 2017/3454; A61B 2017/3458; A61B 2017/346; A61B 2017/348; A61B 2017/3488; A61B 2017/349; A61B 2017/3492; A61B 18/20; A61B 18/22; A61B 18/27; A61B 18/00315; A61B 18/00339; A61B 18/00571; A61B 18/00577; A61B 18/00601; A61B 18/00982; A61B 18/00206; A61B 18/14; A61B 18/147; A61B 18/1487
USPC ... 606/1, 13–16, 53, 79, 167, 170, 176, 179; 600/101, 104, 108, 109–114, 123, 600/128–130, 153, 156, 160
See application file for complete search history.

(56) References Cited

U.S. PATENT DOCUMENTS 6,572,563 B2 * 6/2003 Ouchi ................ A61B 10/0275
 600/564
8,734,435 B2 * 5/2014 Greenberg ............. A61B 18/24
 600/104
9,474,577 B2 * 10/2016 Greenberg ............. A61B 18/22

* cited by examiner

ABLATION CANNULA AND KIT WITH INSERT

CROSS REFERENCE TO RELATED APPLICATIONS

This patent application claims the benefit under 35 U.S.C. § 121 as a continuation of U.S. patent application Ser. No. 14/287,369, filed May 27, 2014, which is a continuation-in-part of U.S. patent application Ser. No. 13/770,859, filed Feb. 19, 2013, now U.S. Pat. No. 8,734,435 entitled DUAL PORT ABLATION CANNULA AND KIT, which is a continuation-in-part of U.S. patent application Ser. No. 11/101,221, filed Apr. 7, 2005 now U.S. Pat. No. 8,376,931 entitled VISUALIZING ABLATION CANNULA, the entire teachings of each which are incorporated herein by reference.

BACKGROUND OF THE INVENTION

Field of the Invention

The disclosed invention is in the field of medical devices and procedures. In particular, the disclosed invention pertains to a novel surgical device and its use for ablation of tissues associated with solid anatomical surfaces such as joints.

Description of the Related Art

Lower back pain (LBP) is a common musculoskeletal complaint of industrialized society with a reported 60-90% of the population experiencing at least one episode of LPB per lifetime. As such, LBP is a very common cause of disability in persons younger than 45 years, the second leading reason for visits to primary care physicians, and the most frequent cause of visits to orthopedic surgeons and neurosurgeons. As the most frequently reported work-related injury, LBP is the most costly of all medical diagnoses when the costs of time lost at work, long-term disability and medical and legal expenses are factored in. Over the past century, various structures associated with the spine and back muscles, including the dorsal root ganglia, dura, muscles of the lumbar spine and the facet joints, have been implicated as the source of chronic LBP. Many recent clinical studies implicate facet joints of the spine as the source of pain in LBP. The spine is composed of a series of functional units, each consisting of an anterior segment made up of two adjacent vertebral bodies and the intervertebral disc between them, and the posterior segment consisting of the laminae and their processes. Bones of the spine articulate anteriorly by intervertebral discs and posteriorly by paired joints. The paired joints, known as the facet or zygapophyseal joints, are formed by the articulation of the processes on the laminae of adjacent vertebrae. Thus the superior articular process of one vertebra articulates with the inferior articular process of the vertebra below to form the facet joint.

Facet joints are true synovial joints with a joint space, hyaline cartilage surfaces, a synovial lining, and a fibrous capsule. Nociceptive (pain-sensing) nerve fibers and autonomic nerves have been identified in the lumbar facet joint capsule and synovial folds in recent studies. Inflammation, injury, nerve entrapment and degenerative osteoarthritic changes in the joint tissues all can lead to pain originating in the facet joints. Facet joint pain may also arise secondary to vertebral disc degeneration, owing to facet-joint osteoarthritis that develops in response to the primary disc degeneration.

Pain cannot be felt if the nerve pathways that relay pain impulses to the brain are interrupted. Painful stimuli from the facet joints are carried by the medial branches of the dorsal primary rami. On the theory that facet joint-mediated LBP should not be perceived in absence of intact medial nerve pathways, denervation (neurotomy) of the dorsal medial nerve branch has been advocated for treatment of lumbar facet joint pain. Early methods included destruction of the nerves by injection of neurolysing agents; however in recent years radiofrequency (RF) ablation of these nerves is the most widely used technique for denervation of the facet joints.

The target of a needle used for facet joint nerve ablation in the lumbar region (L1-L4 levels) is the portion of the nerve on the dorsal surface of the transverse process just caudal to the most medial end of the superior edge of the transverse process. The approximate vicinity of the target nerves can be determined using fluoroscopic techniques in subjects lying prone on a fluoroscopy table. Specifically, in the RF ablation procedure, under radiographic guidance, an introducer cannula is positioned in the vicinity of the dorsal medial nerve. Ideally the cannula is positioned alongside the nerve, rather than with its point facing the nerve. Once the position of the cannula appears to be correct, based on the radiographic image and the "feel" of the target tissue, the surgeon introduces an RF electrode via the cannula, with the aim of positioning the electrode alongside the nerve. Following positive stimulation at low voltage that reproduces the subject's pain, an RF lesion is created by passing current through the electrode that raises the tissue temperature to 60-80 degrees centrigrade for 60-90 seconds. This portion of the procedure is quite uncomfortable and calls for judicious use of sedation and analgesics.

Existing devices such as RF probes used for denervation of facet joints are placed by surgeons using radiographic techniques (C-arm fluoroscopy) without the benefit of endoscopic guidance to ensure accurate positioning of the electrodes. In fact, proper placement of the needle tip in the complicated structure of a subject's spine requires great skill by the treating clinician. The needles may need to be withdrawn and re-inserted multiple times. Errors in needle placement and in particular, the slippage of the needle once placed off the facet joint can result in accidental impalement of structures such as the nerve root in the lower spine, presenting a serious medical risk to the subject.

The success of RF denervation procedures varies widely, with a lower end of 9%. Despite improvements in technological approaches and controls incorporated into later clinical assessments of the efficacy of facet joint denervation as a therapy for LBP, there continues to be a wide range of reported success rates. This wide variability in the procedure in the hands of different practitioners suggests unpredictability inherent in the procedure itself. The unpredictability may be a reflection of failure of existing methods to enable sufficiently precise and stabilize localization of the target nerve prior to lesioning, combined with incomplete destruction of the pain-causing nerve fibers by the RF electrode.

BRIEF SUMMARY OF THE INVENTION

Embodiments of the present invention address deficiencies of the art in respect to facet joint ablation needles and provide a novel and non-obvious ablation cannula kit with an insert. The kit includes a trocar and a hollow shaft defining a longitudinal lumen. The shaft has a proximal segment and a distal segment, such that the distal segment includes a distal tip substantially aligned with the shaft to permit passage of the trocar within the hollow shaft. The distal tip also is configured with a tissue-gripping surface in as much as a plane of the tissue-gripping surface is substantially perpendicular to a longitudinal axis of the shaft. The shaft also includes an auxiliary port extending from an exterior surface of the hollow shaft, the auxiliary port defining a hollow passageway into the hollow shaft.

An insert also can be provided. The insert can include a hollow shaft similar in length to the shaft of the cannula but the insert can have an outside diameter less than an inside diameter of the cannula defining the hollow shaft of the cannula. The insert also can include a proximal segment and a distal segment and can be adapted at the distal segment for securement to the proximal segment of the shaft. The insert yet further can include an auxiliary port extending from an exterior surface of the hollow shaft of the insert, the auxiliary port of the insert defining a hollow passageway into the hollow shaft of the insert. Finally, the kit can include a laser fiber that includes a diameter less than an interior diameter of the hollow shaft of the insert so as to permit passage of the laser fiber through the hollow shaft of the insert.

Additional aspects of the invention will be set forth in part in the description which follows, and in part will be obvious from the description, or may be learned by practice of the invention. The aspects of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE SEVERAL VIEWS OF THE DRAWINGS

There are shown in the drawings embodiments which are presently preferred, it being understood, however, that the invention is not limited to the precise arrangements and instrumentalities shown, wherein.

DETAILED DESCRIPTION OF THE INVENTION

The present invention is a medical apparatus and surgical procedure for the ablation of tissue in the body of a subject. The apparatus can include an ablation needle kit. The kit includes an ablation cannula with a tissue-gripping surface at a distal end of the cannula and an auxiliary port extending from an exterior surface of the cannula and providing a passageway into a hollow shaft defined by the cannula. The kit also can include a laser fiber, a trocar and an insert. The insert can be a tube with an outside diameter that is less than the diameter of the hollow shaft of the cannula and with an inside diameter greater than an inside diameter of the laser fiber. Like the cannula, the insert can have an auxiliary port extending from an exterior surface of the insert and providing a passageway into a hollow shaft of the tube.

In use, an irrigation source can be connected to the auxiliary port of the insert, and a suction device can be connected to an auxiliary port of the cannula. The trocar can be inserted into the cannula and secured thereto. The cannula then can be placed at a tissue site requiring treatment, with the trocar occluding the cannula during placement. Once the cannula has been positioned within the body of the subject proximate to the target tissue, the cannula can grip the target tissue with the tissue-gripping surface and the trocar can be removed from the cannula and replaced in the cannula with the insert secured thereto. The laser fiber then can be inserted into the insert to ablate the target tissue during treatment with a medical laser.

Figure 1:
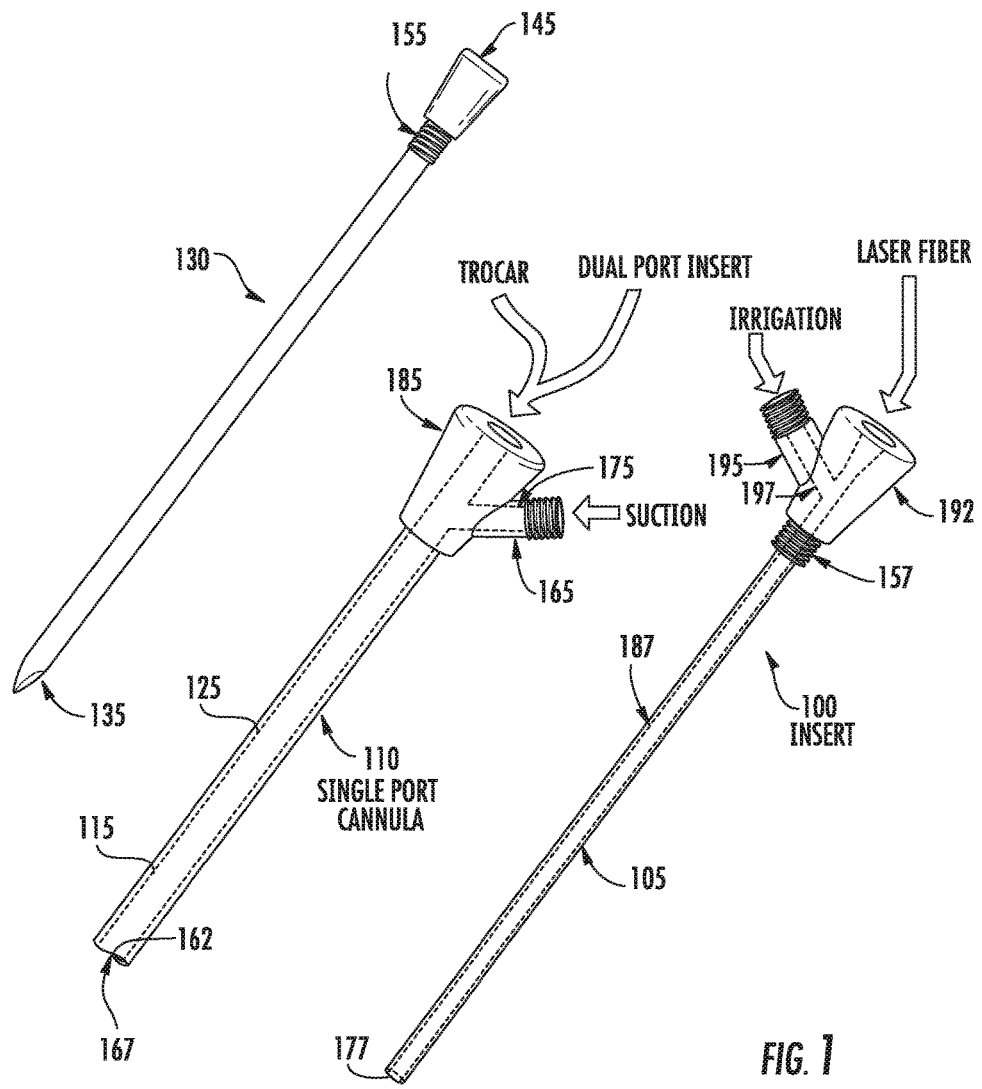
FIG. 1 is a perspective view of a dual port ablation needle with dual port insert.

Referring initially to FIG. 1, several features of the kit of the invention are shown, including an embodiment of the cannula 110. The cannula 110 can include a proximal end 185 and a distal end 167 with an optional tissue-gripping surface 162 defining a hollow shaft 125. A threaded passageway into the hollow shaft 125 can be provided at the proximal end 185 and can be adapted to receive a trocar 130 inserted therethrough and secured thereto by way of complementary threads 155 at a proximal end 145 of the trocar 130. The trocar 130 can be of a length that exceeds that of the cannula 110 such that when inserted and secured thereto, a distal end 135 of the trocar 130 can extend beyond the distal end 167 of the cannula 110. An auxiliary port 165 also can be provided extending from an exterior surface 115 of the cannula 110 and defining a hollow passageway into the hollow shaft 115.

Of note, an insert 100 can be included in the kit. The insert 100 can include an exterior surface 105 defining a tube with a hollow shaft 187 extending from a distal end 177 to a proximal end 192. An auxiliary port 195 can extend from the exterior surface 105 of the insert 100 and can define a hollow passageway 197 into the hollow shaft 187 of the insert 100. Importantly, the outside diameter of the insert 100 can be less than the diameter of the hollow shaft 125 of the cannula so as to permit the insertion of the insert 100 into the hollow shaft 115 of the cannula 110. Preferably, an interstitial space can result between the exterior surface 105 of the insert 100 and the interior walls of the hollow shaft 125 once the insert 100 is inserted into the hollow shaft 125 of the cannula 110 and secured thereto by complementary threading 157.

The lengths of the proximal and distal segments 167, 185 of the cannula 110 can be varied according to the particular application. For example, in a specific embodiment of the invention useful for denervation of facet joints, the narrower distal segment 167 of the cannula 110 can be the only portion inserted into the body of a subject. The "working distance" available for insertion of the cannula 110 beneath the skin can be determined by the length of the distal segment 167. As noted, a tissue-gripping surface 162 can be disposed at the distal segment 167 of the cannula 110. The tissue-gripping surface 162 can include different triangularly shaped tissue-adhering irregular surfaces protruding from the tissue-gripping surface 162. The triangularly shaped tissue-adhering irregular surfaces can be spaced apart from one another. Optionally, each of the triangularly shaped tissue-adhering irregular surfaces can be slightly angled inwards towards a vertex defined by a circumference of a tip of the distal segment 167 so as to inhibit a cutting action of the triangularly shaped tissue-adhering irregular surfaces.

Figure 2:
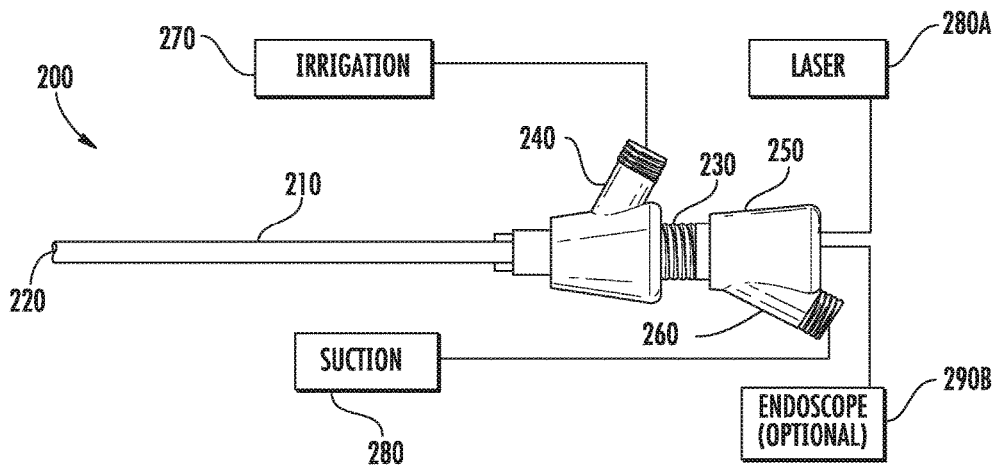
FIG. 2 is a schematic diagram of a dual port ablation probe configured with a dual port insert both connected to a laser, irrigation, suction and optionally, an endoscope; and, FIG. 3 is a flowchart illustrating a procedure for facet joint tissue ablation utilizing a dual port ablation needle kit with dual port insert

The kit described in connection with FIG. 1 can be deployed in an operatory for use in ablation procedures utilizing laser energy and optionally visualization. In further illustration, FIG. 2 is a schematic diagram of an ablation tool 200 that includes an insert 250 disposed within an ablation cannula 210, the tool 200 being connected to each of a laser fiber 290A, irrigation 270, suction 280 and optionally, an endoscope 290B. As shown in FIG. 2, the ablation cannula 210 can include a shaft that is hollow and includes a tissue gripping tip at a distal end 220 of the shaft.

An auxiliary port 240 can extend from an exterior portion of the cannula 210 as well to which irrigation 270 may be attached. The insert 250 may be secured to the ablation cannula 210 by way of coupling 230 and the insert 250 can also include an auxiliary port 260 to which suction 280 may be affixed. As will be recognized by one of skill in the art, the coupling of the irrigation 270 and the suction 280 may alternate as between the auxiliary ports 240, 260 such that irrigation 270 may be affixed to the auxiliary port 260 and suction 280 may be affixed to auxiliary port 240.

Laser fiber 290A may be inserted through insert 250 so as to extend beyond the distal tip 220 of the cannula. Optionally, an endoscope 290B also may be inserted through the insert 250 so as to extend beyond the distal tip 220 of the cannula. To the extent that irrigation 270 is applied to the cannula 210, fluid can travel through the interstitial space defined between the insert 250 and interior wall of the cannula 210 exiting at the distal tip 220 of the cannula. Suction 280 in turn can extract fluid from the distal tip 220 through the hollow shaft of the insert 250 exiting the auxiliary port 260.

Figure 3:
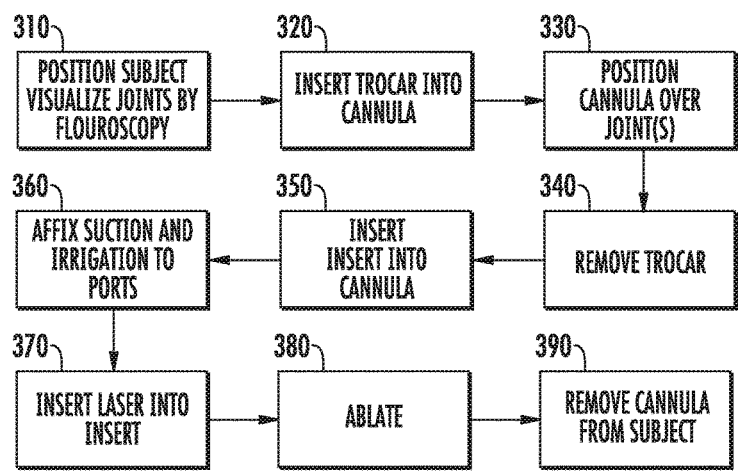

The invention also includes a method of using the visualizing ablation needle set in a surgical procedure for ablation of tissues in a subject's body. As an example of this procedure, a surgeon may achieve denervation of the pain-causing nerve fibers of the facet joints. The steps in a procedure for denervation of facet joints are shown diagrammatically in FIG. 3. Specifically, beginning in step 310, a subject in need of facet joint denervation can be brought to an operating room and placed in the prone position on a radiolucent table. A sterile preparation and drape is performed to the sites of the back to be treated.

A C-arm fluoroscope can be utilized to visualize the involved facet joints. Oblique projections can be used to visualize the ipsilateral side of the facet joints to be treated. Once a facet joint to be treated is identified in this manner, a local infiltrate of anesthetics (e.g. lidocaine with epinephrine) can be administered to the area. In step 320, a small scalpel can then be used to pierce the skin of the identified region. The cannula of the ablation needle kit of the invention, with a trocar positioned within its hollow shaft and secured thereto, can then be advanced through the skin and underlying muscle, and positioned on the facet joint in block 330. The position of the cannula can be photographed and viewed on the screen of the fluoroscope, and adjusted as necessary. Thereafter, pressure can be placed on the cannula. A tissue-gripping surface on the cannula tip can ensure that the cannula, once contacting the facet joint, is stabilized in the appropriate position over the target joint. The trocar can then be disengaged and removed with the right hand while the cannula is held with the left hand In step 340, the trocar can be removed from the cannula and in step 350, the insert can be inserted into the cannula and secured thereto. In step 360, suction and irrigation can be affixed to respectively different auxiliary ports of the cannula and insert. Once the position of the needle is satisfactory, in step 370 a laser fiber connected to a laser energy source can then be passed into the insert and fed through the insert until substantial resistance is felt indicating placement of the laser fiber on the facet joint. Confirmation of proper placement of the needle set for facet denervation is now possible by fluoroscopy and, optionally, by direct visualization using an endoscopic camera also inserted into the insert.

With the cannula thus stabilized on the facet, in step 380, the ablation procedure can be carried out while the area of treatment is irrigated to cool from the action of the laser and outflow can be accomplished by way of the suction device. Duration and energy levels of the laser treatment can be varied according to the particular application. As the facet joint capsule with its associated nerve tissue is ablated, the capsule tissue can be optionally visualized and seen to shrink and disappear. The ability to visualize the extent of tissue ablation while applying the laser beam enables the surgeon to tailor the ablation procedure to the characteristics of individual subjects' facet tissues, thereby ensuring that ablation is both accurate and complete. Finally, in step 390, when the ablation procedure is seen to be satisfactory, the cannula with insert can be removed from the subject.

It should be noted that whereas certain exemplary embodiments of the visualizing ablation needle set and particular clinical applications have been discussed herein, the invention is not so limited, and its scope is to be determined according to the claims set forth below. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

Having thus described the invention of the present application in detail and by reference to embodiments thereof, it will be apparent that modifications and variations are possible without departing from the scope of the invention defined in the appended claims as follows:

We claim:
1. An ablation tool comprising:
   a trocar;
   a cannula comprising a hollow shaft, the hollow shaft of the cannula having a proximal segment and a distal segment, wherein the distal segment comprises a distal tip aligned with the hollow shaft of the cannula to permit passage of the trocar within the hollow shaft of the cannula, and having tissue-adhering irregular surfaces protruding therefrom;
   an auxiliary port extending from an exterior surface of the cannula and defining a hollow passageway into the hollow shaft of the cannula; and,
   an insert comprising an additional hollow shaft and adapted to be inserted into the hollow shaft of the cannula, the insert further comprising an auxiliary port extending from an exterior surface of the insert and defining a hollow passageway into the additional hollow shaft of the insert, the additional hollow shaft comprising an outside diameter of less than an interior diameter of the hollow shaft of the cannula so as to permit passage of a laser fiber through the additional hollow shaft of the insert.

2. The ablation tool of claim 1, wherein the tissue-adhering irregular surfaces are angled inwards towards a vertex defined by a circumference of the distal tip so as to inhibit a cutting action of the tissue-adhering irregular surfaces.

3. The ablation tool of claim 2, wherein the tissue-adhering irregular surfaces are each triangularly shaped.

4. The ablation tool of claim 3, wherein the tissue-adhering irregular surfaces are spaced apart on a circumference of said distal tip.

5. The ablation tool of claim 1, wherein the proximal segment of the shaft is wider than the distal segment.

6. The ablation tool of claim 1, wherein the proximal segment of the shaft is narrower than the distal segment.

7. The ablation tool of claim 1, wherein the insert includes a threaded collar at a distal end of the insert adapted to secure the insert to complementary threads in the distal segment of the cannula.

* * * * *